United States Patent
Savari et al.

(10) Patent No.: US 10,145,775 B2
(45) Date of Patent: Dec. 4, 2018

(54) APPARATUS AND METHODS FOR DETERMINING SWELLING REACTIVITY OF MATERIALS UNDER SUBTERRANEAN WELLBORE CONDITIONS

(71) Applicant: Halliburton Energy Services, Inc., Houston, TX (US)

(72) Inventors: Sharath Savari, Stafford, TX (US); Bhargav Gajji, Pune (IN); Somesh Kurella, Andhra Pradesh (IN)

(73) Assignee: Halliburton Energy Services, Inc., Houston, TX (US)

(*) Notice: Subject to any disclaimer, the term of this patent is extended or adjusted under 35 U.S.C. 154(b) by 198 days.

(21) Appl. No.: 15/022,165

(22) PCT Filed: Oct. 15, 2013

(86) PCT No.: PCT/US2013/065089
§ 371 (c)(1),
(2) Date: Mar. 15, 2016

(87) PCT Pub. No.: WO2015/057208
PCT Pub. Date: Apr. 23, 2015

(65) Prior Publication Data
US 2016/0231220 A1 Aug. 11, 2016

(51) Int. Cl.
*G01N 13/00* (2006.01)
*G01M 15/10* (2006.01)
*G01N 33/24* (2006.01)
*G01N 7/00* (2006.01)

(52) U.S. Cl.
CPC .............. *G01N 13/00* (2013.01); *G01N 7/00* (2013.01); *G01N 33/24* (2013.01)

(58) Field of Classification Search
CPC .......... G01N 13/00; G01N 7/00; G01N 33/24
USPC ......................................................... 73/37.5
See application file for complete search history.

(56) References Cited

U.S. PATENT DOCUMENTS

| | | | |
|---|---|---|---|
| 3,702,564 A | 11/1972 | Chenevert | |
| 4,513,611 A | 4/1985 | Bohlin | |
| 5,275,063 A * | 1/1994 | Steiger | G01N 33/241 73/865.6 |
| 7,240,545 B1 * | 7/2007 | Jennings | G01F 22/00 73/149 |
| 8,434,355 B1 * | 5/2013 | Bi | G01N 15/088 73/152.05 |
| 8,443,661 B1 | 5/2013 | Bi | |
| 2007/0240514 A1 | 10/2007 | Irani et al. | |
| 2009/0306898 A1 * | 12/2009 | Anschutz | G01N 3/10 702/11 |
| 2010/0138158 A1 | 6/2010 | Nutley et al. | |

(Continued)

OTHER PUBLICATIONS

International Search Report and Written Opinion issued in related PCT Application No. PCT/US2013/065089 dated Jul. 9, 2014, 16 pages.

(Continued)

*Primary Examiner* — Natalie Huls
*Assistant Examiner* — Monica S Young
(74) *Attorney, Agent, or Firm* — Tenley Krueger; Baker Botts L.L.P.

(57) ABSTRACT

Methods and apparatuses for determining the swell of a subterranean formation sample when contacted with a fluid at subterranean conditions.

20 Claims, 3 Drawing Sheets

(56) References Cited

U.S. PATENT DOCUMENTS

2011/0232368 A1    9/2011    Al-Dhafeeri et al.

OTHER PUBLICATIONS

Ewy, et al., "Shale Swelling, Osmosis and Acoustic Changes Measured under Simulated Downhole Conditions," SPE Paper 78160, SPE/ISRM Rock Mechanics Conference, Irving, Texas, Oct. 20-23, 2002, 10 pages.
Osisanya et al.,"Physics—Chemical Modeling of Wellbore Stability in Shale Formations" Petroleum Society of CIM & AOSTRA, Paper No. 94-205, 1994, 16 pages.
Bratland, et al., "Linear Position Sensing Using Magnetoresistive Sensors," Paper A2.4, Honeywell, 6 pages.
Application Note AN211—"Applications of Magnetic Position Sensors," Honeywell Sensor Products, 2002, 8 pages.
Wan et al., "High Temperature Linear Position Sensor," Honeywell International Inc., 4 pages.
Datasheet—"Magnetic Displacement Sensors" HMC1501/1512, Honeywell Sensors, 2008, 8 pages.
Linear Swell Meter, Model 2100, Instruction Manual, Fann Instrument Company, 2013, 78 pages.

\* cited by examiner

APPARATUS AND METHODS FOR DETERMINING SWELLING REACTIVITY OF MATERIALS UNDER SUBTERRANEAN WELLBORE CONDITIONS

CROSS-REFERENCE TO RELATED APPLICATION

The present application is a U.S. National Stage Application of International Application No. PCT/US2013/065089 filed Oct. 15, 2013, which is incorporated herein by reference in its entirety for all purposes.

TECHNICAL FIELD

This application is in the field of producing crude oil or natural gas from subterranean formations. More specifically, the application generally relates to methods and apparatuses for determining surface wetting under subterranean wellbore conditions.

BACKGROUND ART

To produce oil or gas, a well is drilled into a subterranean formation that is an oil or gas reservoir.

Generally, well services include a wide variety of operations that may be performed in oil, gas, geothermal, or water wells, such as drilling, cementing, completion, and intervention. Well services are designed to facilitate or enhance the production of desirable fluids such as oil or gas from or through a subterranean formation. A well service usually involves introducing a well fluid into a well.

As used herein, a "well fluid" broadly refers to any fluid adapted to be introduced into a well for any purpose. A well fluid can be, for example, a drilling fluid, a cement composition, a treatment fluid, or a spacer fluid.

Drilling fluids, also known as drilling muds or simply "muds," are typically classified according to their base fluid (that is, the continuous phase). A water-based mud ("WBM") has solid particulate (e.g., clays, bulk density increasing agents, lost circulation materials,) suspended in an aqueous liquid as the continuous phase. The water can be brine. A brine-based drilling fluid is a water-based mud in which the aqueous component is brine. In some cases, oil maybe emulsified in a water-based drilling mud. An oil-based mud ("OBM") has solid particulate suspended in oil as the continuous phase. In some cases, an aqueous phase of water or brine is emulsified in the oil. Drill cuttings from the formation will be the additional solid particulates getting suspended in both oil-based and water based muds as the drilling process begins.

As used herein, the word "treatment" refers to any treatment for changing a condition of any portion of a wellbore or an adjacent subterranean formation; however, the word "treatment" does not necessarily imply any particular treatment purpose. A treatment usually involves introducing a well fluid for the treatment, in which case it may be referred to as a treatment fluid, into a well. As used herein, a "treatment fluid" is a fluid used in a treatment. The word "treatment" in the term "treatment fluid" does not necessarily imply any particular treatment or action by the fluid.

As used herein, the terms spacer fluid, wash fluid, and inverter fluid can be used interchangeably. A spacer fluid is a fluid used to physically separate one special-purpose fluid from another. It may be undesirable for one special-purpose fluid to mix with another used in the well, so a spacer fluid compatible with each is used between the two. A spacer fluid is usually used when changing between well fluids used in a well.

For example, a spacer fluid is used to change from a drilling fluid during drilling to cement composition during cementing operations in the well. In case of an oil-based drilling fluid, it should be kept separate from a water-based cementing fluid. In changing to the latter fluid, a chemically treated water-based spacer fluid is usually used to separate the drilling fluid from the water-based cementing fluid.

A spacer fluid specially designed to separate a special purpose oil-external fluid from a special purpose water-external fluid may be termed as an inverter fluid. Inverter fluids may be so designed that the diffused contaminated layer between both the special purpose fluids has progressive variation in properties like solids carrying capability, electrical conductivity, rheology, and chemical potential.

Drilling is the process of drilling the wellbore. After a portion of the wellbore is drilled, sections of steel pipe, referred to as casing, which are slightly smaller in diameter than the borehole, are placed in at least the uppermost portions of the wellbore. The casing provides structural integrity to the newly drilled borehole.

While drilling an oil or gas well, a drilling fluid is circulated downhole through a drillpipe to a drill bit at the downhole end, out through the drill bit into the wellbore, and then back uphole to the surface through the annular path between the tubular drillpipe and the borehole. The purpose of the drilling fluid is to maintain hydrostatic pressure in the wellbore, lubricate the drill string, and carry rock cuttings out of the wellbore.

Drilling fluids are typically classified according to their base material. In oil base fluids, solid particles are suspended in oil, and water or brine may be emulsified with the oil. The oil is typically the continuous phase. In water base fluids, solid particles are suspended in water or brine, and oil may be emulsified in the water. The water is typically the continuous phase.

Drilling and service fluids, such as drilling mud, cementing spacer fluids and the like, can have undesirable effects on hydrocarbon bearing subterranean formation materials. Shale and clay formations can swell in the present of certain liquids closing off the pores in the formation and reducing hydrocarbon flow through the formation.

Generally, the greater the depth of the formation, the higher the static temperature and pressure of the formation. The swelling effect of well fluids on formation materials vary chemically and physically with the well conditions, such as, temperature and pressure at subterranean locations.

It would be highly desirable in well operations to have apparatuses and methods for determining the swelling effects of well fluids on formation materials at subterranean wellbore temperature, pressure and other conditions. Applications include, for example, the designing of well fluids for a particular formation material.

SUMMARY OF THE DISCLOSURES

According to this disclosure, methods and apparatuses are provided for determining swelling of a formation material in the present of a liquid under wellbore conditions. In general, the methods and apparatuses are disclosed herein include measuring swelling effects on formation samples while simulating downhole conditions.

These and other aspects of the disclosure will be apparent to one skilled in the art upon reading the following detailed description. While the disclosed methods and apparatuses are susceptible to various modifications and alternative forms, specific embodiments thereof will be described in detail and shown by way of example. It should be understood, however, that it is not intended to limit the disclosure to the particular forms disclosed, but, on the contrary, the intent of the disclosure is to cover all modifications and alternatives falling within the spirit and scope as expressed in the appended claims.

BRIEF DESCRIPTION OF THE DRAWING

The accompanying drawings are incorporated into the specification to help illustrate examples described herein.

DETAILED DESCRIPTION OF EMBODIMENTS

Figure 1:
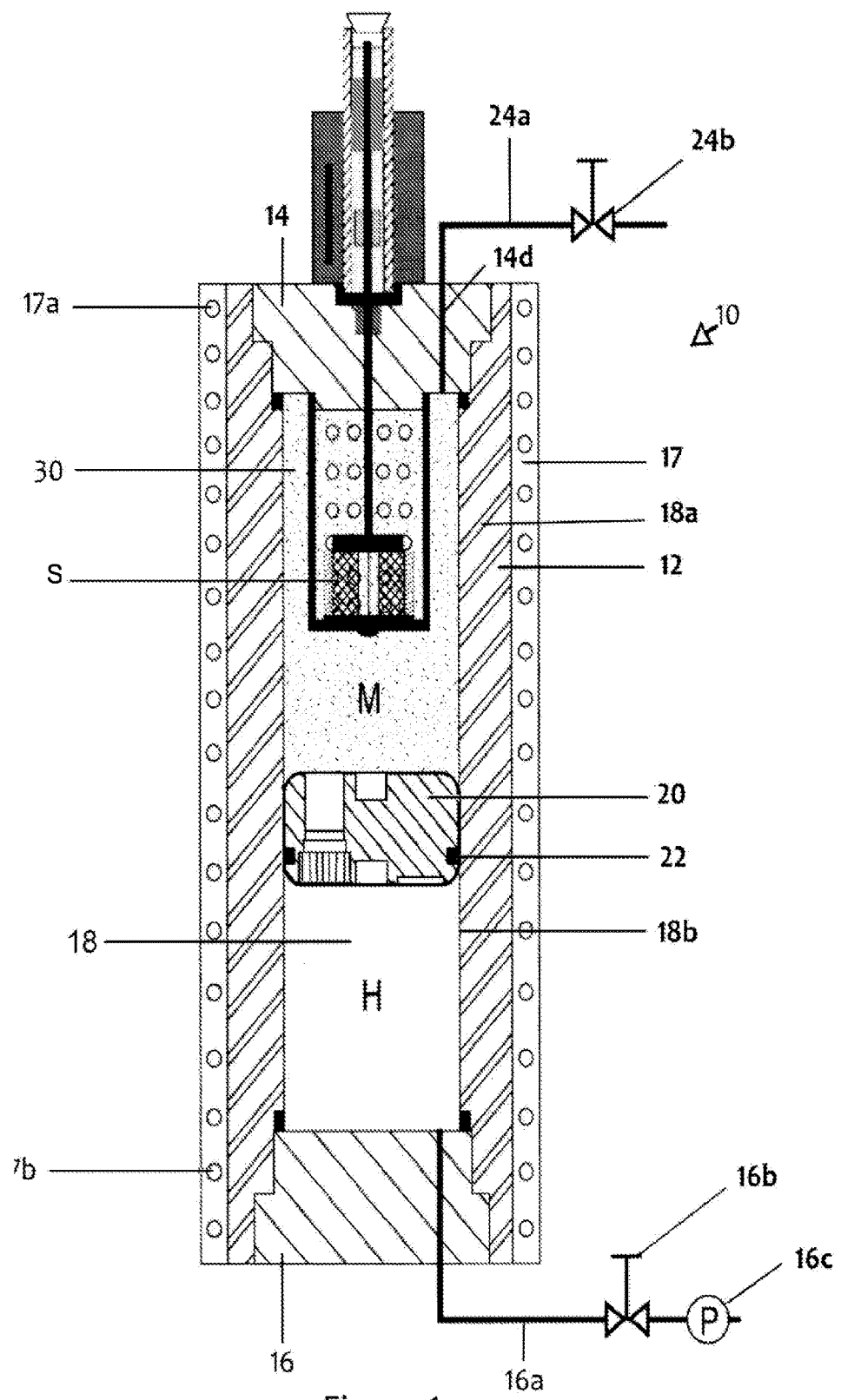
FIG. 1 is a longitudinal cross-section view of an apparatus for measuring sample swelling under wellbore conditions according to the present invention.

The apparatus 10 and methods for determining swelling characteristics of materials under subterranean wellbore conditions will be described by reference to FIGS. 1-3, wherein like reference characters are used to designate like or corresponding parts throughout the several figures. An expansion of a material sample is measured while located in a chamber in the apparatus and while being exposed to a well fluid at subterranean wellbore conditions as high as 450° F. and 12,000 psi. If the apparatus is to be used to test the expansion of shale materials then the apparatus 10 need only withstand the pressures and temperature where shale is found (for example at least about 5000 psi and 400° F.)

The apparatus 10 comprises a cylindrical housing 12 closed at its upper and lower ends by end caps 14 and 16, respectively, to forma sealed cylindrical chamber 18. End caps 14 and 16 are connected to the housing 12 by threads or other suitable means. At least the upper end cap 14 is removably attached to provide access to the chamber 18. In the present embodiment end caps 14 and 16 each have fluid passageways communicating with the interior of chamber 18. The fluid passageway in end cap 14 is connected to a fluid conduit 24a and valve 24b. The fluid passageway in end cap 16 is connected to a fluid conduit 16a, valve 16b and pump 16c. These passageways allow fluids to be added to and removed from the chamber 18. The pump 16c can be used to bring chamber 18 up to desired wellbore pressures. The various components of the apparatus 10 are preferably designed to withstand pressures as high as about 12,000 psi to simulate actual wellbore conditions.

A cylindrical electrically powered heating jacket 17 abuts in conductive thermal contact the outside wall of housing 12. Leads 17a and 17b are used to supply electrical power to the jacket 17. The jacket 17 can be used to regulate the temperature of fluids in the chamber 18 and to replicate subterranean wellbore conditions. The various components of the apparatus 10 are preferably designed to withstand temperatures as high as about 450° F. to simulate actual wellbore conditions.

A cylindrical piston assembly 20 with an annular sliding seal 22 is mounted to axially reciprocate in the chamber 18. Piston 20 divides the chamber 18 into an upper variable volume chamber 18a and a lower variable volume chamber 18b. An annular seal 22 on the piston in the form of an O-ring or packing seals against the interior walls of the chamber 18. The piston functions to isolate the test fluid from the pressuring fluid.

A core sample mounting assembly 30 is removably suspended in upper chamber 18a by threads 72 on the inside of the upper end cap 14. As will be described in detail herein, a well fluid "M", such as for example, a drilling mud "M" is placed in upper chamber 18a in fluid contact with a core sample "S" mounted in core mounting assembly 30. An oil, such as, mineral oil or hydraulic fluid, "H" is pumped into lower chamber 18b. The pressure in chamber 18b is raised by pump 16c to the test pressure while this test pressure is applied through piston 20 to the well fluid "M" and sample in chamber 18a.

Figure 2:
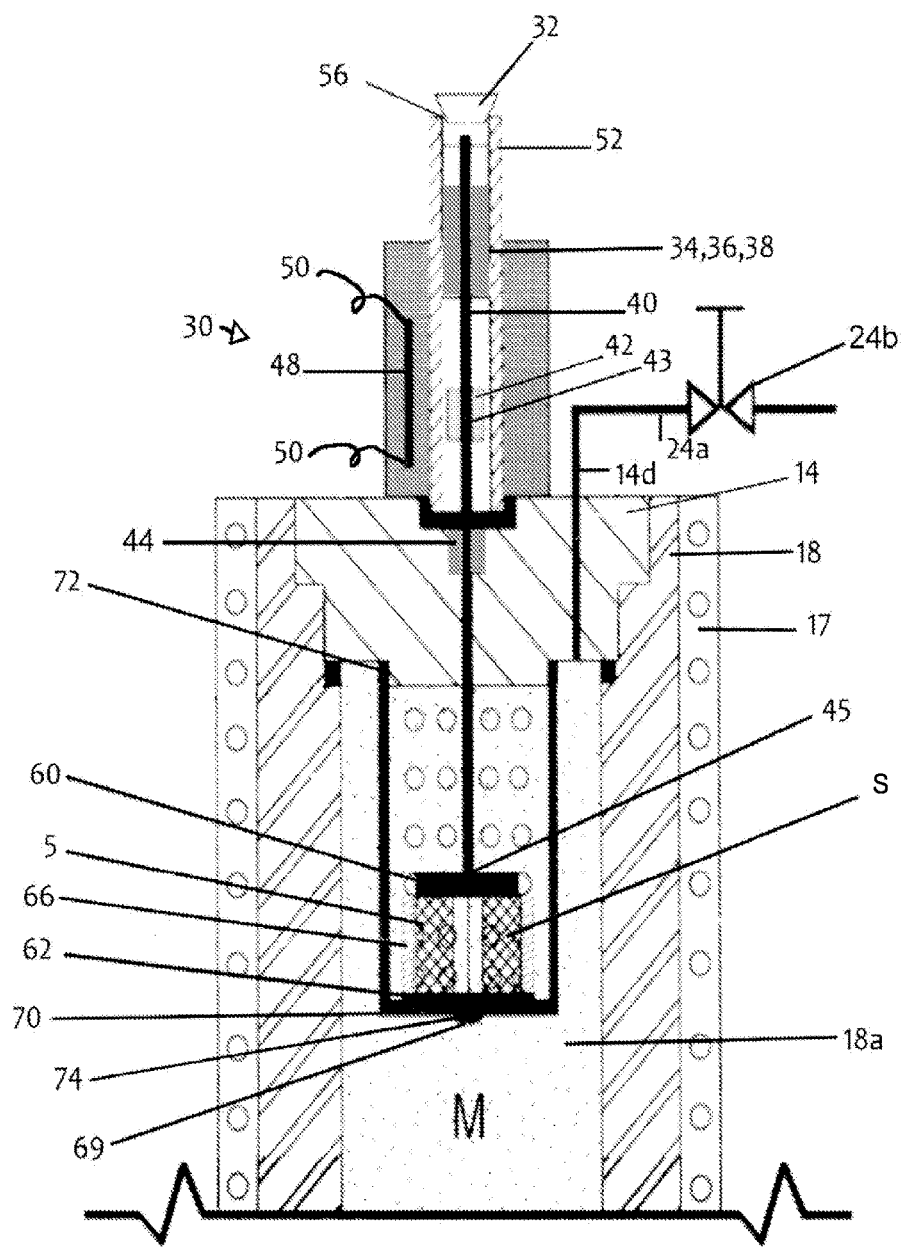
FIG. 2 is an enlarged view of a portion of the apparatus illustrated in FIG. 1.
Figure 3:
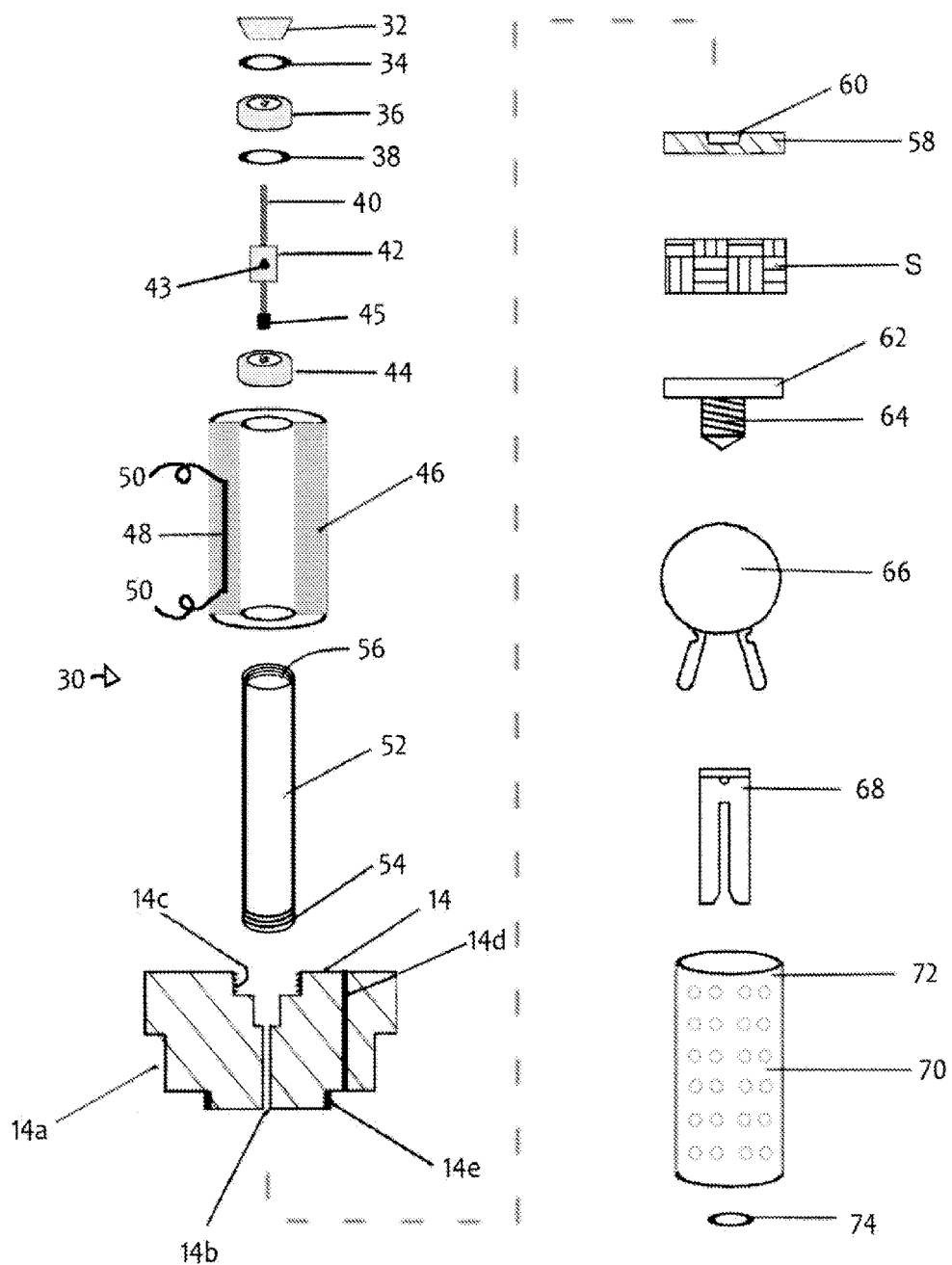
FIG. 3 is an exploded view of the apparatus illustrated in FIG. 1.

The detail structure for mounting and testing the swell in the sample S is best illustrated in FIGS. 2 and 3. The sample S in the current embodiment is cylindrical shaped. The sample S is prepared by pulverizing using a conventional procedure and an LSM compactor. If core sample exist, it can be easily formed into a cylinder for swell testing without powdering it. However, other shapes could be used. If the subterranean formation to be tested is a shale material then the sample can be prepared using an LSM Compactor in a conventional procedure. A core sample holder comprises a bottom or lower disk 62 and a top or upper disk 58. The upper and lower disks have a diameter that corresponds to the diameter of the core sample S. A cylindrical core holder 66 has body of mesh material formed into a cylindrical shape of a size to fit around the outer cylindrical wall of the sample S. The sample S is mounted for testing between the upper and lower disks 58 and 62, respectively, with the planar circular shaped faces of the sample S abutting the disks. If the sample is formed from granular material, holder 66 is placed around the cylindrical wall of the sample S with the holder is held in contact with the outer walls by clip 68. The sample S is held together in the cylindrical shape by the mesh of holder 66. The disks 58 and 62 cover the faces and as will be explained, fluid contact with the sample is at the cylinder wall. The openings in the mesh provide fluid flow paths for test fluid to contact the sides of the sample S.

The assembled sample S is placed in the bottom of a perforated cylinder 70 with the lower disk 62 in contact with the bottom wall of the perforated cylinder 70. The cylinder 70 has an open internally threaded top 72. As illustrated lower disk 62 has a shaft 64, which extends through a central opening (not shown) in the bottom wall of the cylinder 70. A snap ring 74 is affixed to the shaft 64 to mount the sample assembly within the cylinder 70.

The cylinder 70 with the sample inside is connected, as shown in FIG. 2, to the underside of the upper end cap 14 by threaded engagement between the external threads 14e and the internal threads on end 72 of the perforated cylinder 70. External threads 14a are used to connect the upper end cap 14 to the chamber 18. Conventional annular seals are present to seal the junction between the end cap 14 in the chamber 18.

Next an open-ended cylinder 52 utilizes threads on its lower end 54 to connect to the end cap 14 via internal threads 14c. Conventional annular seals (not shown) are provided to seal the threaded joint between cylinder 52 and end cap 14. The upper end of the cylinder 52 is internally threaded at 56 for receiving a threaded plug 32 to seal the upper end of the cylinder 52. Appropriate annular seals (not shown) are present to seal the joint between the plug 32 and cylinder 52.

An annular shaped rod guide 44 is mounted in a recess in the upper surface of the end cap 44. An elongated non-magnetic metallic shaft 40 (preferably stainless steel) is externally threaded at end 45. These threads are of a size and shape mate with the internally threaded recess 60 in the upper surface of top disk 58. The shaft 40 is positioned to extend through the end cap 14 and guide 44 into contact with the top disk 58. The upper end of the shaft 40 extends through and is held in position by a second annular shaped rod guide 36. Rod guide 36 is held in axial position in the cylinder 52 by a pair of snap rings 34 and 38.

Shaft 40 is rotated to mesh threads 45 with the threads in recess 40. It should be understood of course that the shaft 40 could be installed either prior to or after installation of the cylinder 52. A position reference member 42 is movably attached to the shaft 40 by a grub screw 43. Once the shaft 40 is been connected to the top disk 60 the position reference member 42 can be properly positioned axially on shaft 40 and locked in position by contact between the grub screw 43 and shaft 40.

As will be appreciated, when the sample S is exposed the well fluid in upper chamber 18a, swelling of the sample will cause the top and bottom disks 58 and 62, respectively, to spread apart. Accordingly, shaft 40 and position reference 42 will be displaced upward (toward the top of the page as illustrated in FIG. 2) a distance corresponding to the change in thickness of the sample.

To measure movement of the shaft and position reference 42, a sensor 48 is mounted adjacent to the exterior of the cylinder 52 and aligned axially with the position reference member 42. The sensing mechanism use is preferably a non-contact displacement measurement. Non-contact is preferred because it reduces measurement errors due to friction. The sensor is mounted in a surrounding cylinder 52 which should be made from thermally insulating non-magnetic material (wood or plastic) to protect the sensor from the heat. The sensor 48 has electric leads 50. The current and voltage of the signal in the leads can be used to determine the initial position of the reference member 42 and the change of position of the reference member 42 due to swelling of the sample S. According to one embodiment, the position reference could be a magnet with the sensor continuously sensing the magnets position thru changes in inductance. In another embodiment, the position reference piece could comprise a strong dielectric material that changes in capacitance at this sensor as it moves due to swelling of the sample. A data acquisition system (not shown) is connected to the sensor to record the sample's swelling data.

In one example, the sample S is mounted in the upper chamber 18a and the position of the reference member 42 is recorded. A well fluid M is pumped through conduit 24a and into the upper chamber 18a via passageway 14d in the upper end cap 14. Next, a hydraulic fluid such as mineral oil (or another suitable fluid) is pumped through valve 16b and conduit 16a and into chamber 18. With valve 24b open and plug 32 removed piston 20 will move toward the upper end cap 14 causing any gas in chamber 18 to be vented through cylinder 52 and valve 24b. Once any gas in the chamber 18a is vented, valve 24b is closed and plug 32 installed to seal chamber 18. Pump 16c is used to increase the pressure of the well fluid and the heating jacket 17 is engaged to raise the temperature of the well fluid contacting the sample S. Other peripheral equipment can be provided including: pressurizing apparatus for example a hand oil pump or nitrogen source; pressure regulators; valves; temperature controllers; thermocouples and the like (not illustrated).

According to an embodiment, a method is provided including the steps of:

(A) obtaining or providing a sample of a subterranean formation material:
(B) placing the formation material sample in an enclosed chamber;
(C) placing a well fluid in the chamber in contact with the formation material sample; and
(D) controlling the pressure and temperature of the well fluid in the chamber to a temperature and a pressure corresponding to a subterranean well location while measuring the linear swelling of the sample.

According to another embodiment of this method, the step of control or controlling of a pressure or temperature condition includes any one or more of maintaining, applying, or varying of the condition. For example, controlling the temperature of a substance can include maintaining an initial temperature, heating, or cooling.

According to an embodiment of this method, the step of control or controlling of a pressure or temperature condition includes maintaining the pressure above 5000 psi.

According to an embodiment of this method, the step of control or controlling of a pressure or temperature condition includes maintaining the temperature above 400 degrees Fahrenheit.

According to an embodiment of this method, it additionally includes the steps of selecting a formation material sample with opposed spaced faces and measuring the change in distance between the faces before and after the sample is contacted by the well fluid.

According to an embodiment, the method additionally includes obtaining the formation material sample comprising a shale material.

According to an embodiment, the method additionally includes obtaining the formation material sample from a subterranean location and the pressure and temperature maintaining step comprises maintaining the well fluid at the temperature and pressure of the formation from which the formation sample was obtained.

According to an embodiment of this method, the well fluid comprises cement material.

According to yet another embodiment of this method, the well fluid comprises oil-based drilling mud.

According to an embodiment of this method, the well fluid comprises water-based drilling mud.

According to an embodiment of this method, the well fluid comprises spacer fluid.

According to an embodiment, a method for selecting a well fluid for use in a well intersecting a subterranean formation material having a temperature and pressure including the steps of:

(A) obtaining or providing a sample of the subterranean formation material;
(B) placing the formation material sample in an enclosed chamber;
(C) placing a first well fluid in the chamber in contact with the formation material sample;
(D) controlling the pressure and temperature of the well fluid in the chamber to the temperature and a pressure corresponding to a subterranean well location while measuring the linear swelling of the sample;
(E) repeating steps B, C and D while contacting another sample of the formation material with a second well fluid; and
(F) selecting a well fluid for use in drilling the well based on the liner swelling measurements.

According to an embodiment, an apparatus for testing the expansion of a sample of formation material comprising:

(A) a container forming an enclosed chamber containing a well fluid;
(B) a formation material sample in the chamber in contact with the well fluid;
(C) a sample support in the chamber supporting the formation material sample;
(D) a well fluid temperature heater for raising the temperature of the well fluid in the chamber;
(E) a thermostat for measuring the temperature of the fluid in the chamber;
(F) pump connected to the chamber for raising the pressure of the well fluid in the chamber;
(G) pressure sensor for measuring the pressure of the fluid in the chamber; and
(H) an indicator in contact with the sample to move as the formation material sample expands.

According to an embodiment, an apparatus is provided including a piston in the chamber sealed against the walls of the chamber and dividing the chamber into first and second variable volume chambers.

According to an embodiment of this apparatus, wherein the formation sample and well fluid is located in the first variable volume chamber.

According to an embodiment of this apparatus, wherein a hydraulic fluid is placed in the second variable volume chamber.

According to an embodiment of this apparatus, wherein the well fluid comprises cement material.

According to an embodiment of this apparatus, wherein the well fluid comprises oil based drilling mud.

According to an embodiment of this apparatus, wherein the well fluid comprises water based drilling mud.

According to an embodiment of this apparatus, wherein the well fluid comprises spacer fluid.

According to an embodiment of this apparatus, wherein the formation sample has opposed parallel surfaces.

The words or terms used herein have their plain, ordinary meaning in the field of this disclosure, except to the extent explicitly and clearly defined in this disclosure or unless the specific context otherwise requires a different meaning.

If there is any conflict in the usages of a word or term in this disclosure and one or more patent(s) or other documents that may be incorporated by reference, the definitions that are consistent with this specification should be adopted.

The words "comprising," "containing," "including," "having," and all grammatical variations thereof are intended to have an open, non-limiting meaning. For example, a composition comprising a component does not exclude it from having additional components, an apparatus comprising a part does not exclude it from having additional parts, and a method having a step does not exclude it from having additional steps. When such terms are used, the compositions, apparatuses, and methods that "consist essentially of" or "consist of" the specified components, parts, and steps are specifically included and disclosed.

The indefinite articles "a" or "an" mean one or more than one of the component, part, or step that the article introduces.

Terms such as "first," "second," "third," etc. are assigned arbitrarily and are merely intended to differentiate between two or more components, parts, or steps that are otherwise similar or corresponding in nature, structure, function, or action. For example, the words "first" and "second" serve no other purpose and are not part of the name or description of the following name or descriptive terms. The mere use of the term "first" does not require that there be any "second" similar or corresponding component, part, or step. Similarly, the mere use of the word "second" does not require that there by any "first" or "third" similar or corresponding component, part, or step. Further, it is to be understood that the mere use of the term "first" does not require that the element or step be the very first in any sequence, but merely that it is at least one of the elements or steps. Similarly, the mere use of the terms "first" and "second" does not necessarily require any sequence. Accordingly, the mere use of such terms does not exclude intervening elements or steps between the "first" and "second" elements or steps, etc.

To replicate the downhole conditions and to carry out meaningful testing, a concentration ratio needs to be first fixed and hence, the electrolyte is chosen to be a mixture of an oil-based well fluid and a water-based well fluid in the desired concentration. The water-based well fluid can have a known concentration of surfactant package already pre-mixed.

Therefore, the present disclosure is well adapted to attain the ends and advantages mentioned as well as those that are inherent therein.

The particular embodiments disclosed above are illustrative only, as the present disclosure may be modified and practiced in different but equivalent manners apparent to those skilled in the art having the benefit of the teachings herein. It is, therefore, evident that the particular illustrative embodiments disclosed above may be altered or modified and all such variations are considered within the scope and spirit of the present disclosure.

The various elements or steps according to the disclosed elements or steps can be combined advantageously or practiced together in various combinations or sub-combinations of elements or sequences of steps to increase the efficiency and benefits that can be obtained from the disclosure.

The disclosure illustratively disclosed herein suitably maybe practiced in the absence of any element or step that is not specifically disclosed or claimed.

Furthermore, no limitations are intended to the details of construction, composition, design, or steps herein shown, other than as described in the claims.

What is claimed is:

1. A method of measuring the swelling effects of a fluid on a sample of a subterranean formation at well condition present at a subterranean location where the formation is located, comprising the steps of:
    a. dividing a chamber into an upper variable volume chamber and a lower variable volume chamber using a piston mounted to axially reciprocate in the chamber;
    b. providing a sample of a subterranean material inside a first cylinder;
    c. enclosing the sample in a holder between an upper disk and a lower disk of the holder, wherein the lower disk of the holder contacts a bottom of the first cylinder of the upper variable volume chamber, and wherein the holder comprises a body of mesh;
    d. connecting the first cylinder and a second cylinder to an upper end cap of the upper variable volume chamber, wherein the upper end cap is between the first cylinder and the second cylinder;
    e. extending a shaft through the upper disk and the upper end cap into the second cylinder;
    f. attaching a reference to a portion of the shaft within the second cylinder;
    g. aligning a sensor with the reference;
    h. pressurizing the lower variable volume chamber with a pressuring fluid;

i. isolating, by the piston, a fluid in the upper variable volume chamber from the pressuring fluid in the lower variable volume chamber;

j. contacting the sample in the upper variable volume chamber with the fluid;

k. replicating in the chamber the well condition present at a subterranean location whereby the sample is contacted by the fluid at the well condition at the subterranean location; and l. measuring the swell in the sample while contacted by the fluid at the well condition at the subterranean location based on one or more measurements from the sensor.

2. The method according to claim 1, wherein the well condition at which the measuring step is performed comprises at least one of the pressure present at the subterranean location and the temperature present at the subterranean location.

3. The method according to claim 2, wherein the measuring step is performed at pressures elevated above atmospheric pressure.

4. The method according to claim 2, wherein the measuring step is performed at pressures at or above 5000 psi.

5. The method according to claim 2, wherein the measuring step is performed at temperatures elevated above atmospheric temperature.

6. The method according to claim 2, wherein the measuring step is performed at temperatures or below 450° F.

7. The method according to claim 2, wherein the measuring step is performed at temperatures elevated above atmospheric temperature and at pressures elevated above atmospheric pressure.

8. The method according to claim 1, wherein the steps of contacting the sample in the chamber with a fluid comprises selecting a well fluid and placing the selected well fluid in the chamber.

9. The method according to claim 8, wherein the well fluid comprises at least one fluid selected from the group consisting of water based drilling mud, hydrocarbon based drilling mud, drilling fluid, cement composition, treatment fluid, and spacer fluid.

10. The method according to claim 1, wherein the step measuring the swell in the sample comprises measuring the change in distance between opposed parallel surfaces on the sample.

11. The method according to claim 10, wherein the sample is generally cylindrical shaped with circular opposed parallel end surfaces and a cylindrical side surface.

12. The method according to claim 11, wherein the sample is contacted by the fluid on its cylindrical side.

13. The method according to claim 11, wherein the first cylinder threadedly engages the upper end cap.

14. The method according to claim 13, wherein the shaft extends through a rod guide mounted in a recess of the upper end cap.

15. The method according to claim 1, wherein the step of measuring the swell in the sample comprises forming opposed parallel top and bottom surfaces on the sample and measuring the change in distance between opposed top and bottom surfaces after contacting side surfaces of the sample with well fluid under the well condition.

16. The method according to claim 1, wherein the step of measuring the swell in the sample comprises contacting the sample with the reference and sensing the movement of the preference.

17. An apparatus for measuring the swelling effects of a fluid on a sample of a subterranean formation at pressures and temperatures present at a subterranean location where the formation is located, comprising:

a. a container having walls forming a sealed chamber for containing the fluid in a first portion of the chamber;

b. a first cylinder of the first portion of the chamber, wherein the sample is in the first cylinder;

c. a holder comprising a body of mesh that fits around the sample, wherein the sample is between an upper disk and a lower disk of the holder, and wherein the lower disk of the holder contacts a bottom of the first cylinder;

d. an upper end cap of the first portion of the chamber that connects to the first cylinder and a second cylinder, wherein the upper end cap is between the first cylinder and the second cylinder;

e. a shaft that extends through the upper disk and the upper end cap into the second cylinder;

f. a reference attached to a portion of the shaft within the second cylinder;

g. a sensor mounted to the second cylinder and aligned with the reference that senses a position of the reference;

h. a pump operably associated with the fluid to pressurize the fluid in the first portion of the chamber using a pressuring fluid in a second portion of the chamber to an elevated pressure present at a subterranean location where the formation is located;

i. a piston assembly between the fluid and the pressuring fluid, wherein the piston assembly isolates the fluid from the pressuring fluid; and j. a heater operably associated with the fluid to heat the fluid to an elevated temperatures present at a subterranean location where the formation is located.

18. The apparatus of claim 17 wherein the reference comprises magnetic material and the sensor comprises an inductance sensor.

19. The apparatus of claim 17 wherein the reference comprises dielectric material and the sensor comprises a capacitance sensor.

20. The apparatus of claim 17 wherein the reference is spaced away from contact with the sensor.

* * * * *